US008889592B2

(12) United States Patent
Fischer et al.

(10) Patent No.: US 8,889,592 B2
(45) Date of Patent: Nov. 18, 2014

(54) INSECTICIDAL AND/OR HERBICIDAL COMPOSITION HAVING IMPROVED ACTIVITY BASED ON SPIROHETEROCYCLICALLY SUBSTITUTED TETRAMIC ACID DERIVATIVES

(75) Inventors: Reiner Fischer, Monheim (DE); Stefan Lehr, Liederbach (DE); Olga Malsam, Rosrath (DE); Rolf Pontzen, Leichlingen (DE); Elmar Gatzweiler, Budingen (DE); Rainer Sussmann, Limburg (DE)

(73) Assignee: Bayer CropScience AG, Monheim (DE)

( * ) Notice: Subject to any disclaimer, the term of this patent is extended or adjusted under 35 U.S.C. 154(b) by 518 days.

(21) Appl. No.: 13/090,759

(22) Filed: Apr. 20, 2011

(65) Prior Publication Data

US 2011/0281727 A1 Nov. 17, 2011

Related U.S. Application Data

(60) Provisional application No. 61/325,893, filed on Apr. 20, 2010.

(30) Foreign Application Priority Data

Apr. 20, 2010 (EP) .................................... 10160451

(51) Int. Cl.
| | | |
|---|---|---|
| A01N 43/90 | (2006.01) | |
| A01N 33/02 | (2006.01) | |
| A01N 33/12 | (2006.01) | |
| A01N 57/20 | (2006.01) | |
| A01N 59/00 | (2006.01) | |
| A01N 59/26 | (2006.01) | |
| A01N 47/06 | (2006.01) | |

(52) U.S. Cl.
CPC ................ *A01N 33/12* (2013.01); *A01N 43/90* (2013.01); *Y10S 514/946* (2013.01)
USPC ............. 504/130; 504/123; 504/128; 514/75; 514/112; 514/278; 514/642; 514/946; 424/710; 424/713; 424/719; 424/720

(58) Field of Classification Search
USPC ............ 514/278, 75, 112, 642, 946; 424/710, 424/713, 719, 720; 504/123, 128, 130
See application file for complete search history.

(56) References Cited

U.S. PATENT DOCUMENTS

| | | | |
|---|---|---|---|
| 2,842,476 | A | 7/1958 | Schreiber |
| 4,844,734 | A | 7/1989 | Iwasaki et al. |
| 4,888,049 | A | 12/1989 | Iwasaki et al. |
| 4,985,063 | A | 1/1991 | Fischer et al. |
| 5,045,560 | A | 9/1991 | Fischer et al. |
| 5,116,836 | A | 5/1992 | Fischer et al. |
| 5,225,434 | A | 7/1993 | Bertram et al. |
| 5,258,527 | A | 11/1993 | Krauskopf et al. |
| 5,462,912 | A | 10/1995 | Hioki et al. |
| 5,462,913 | A | 10/1995 | Fischer et al. |
| 5,504,057 | A | 4/1996 | Fischer et al. |
| 5,538,937 | A | 7/1996 | Hasebe et al. |
| 5,567,671 | A | 10/1996 | Fischer et al. |
| 5,589,469 | A | 12/1996 | Fischer et al. |
| 5,622,917 | A | 4/1997 | Fischer et al. |
| 5,683,965 | A | 11/1997 | Bachmann et al. |
| 5,705,476 | A | 1/1998 | Hoffarth |
| 5,792,755 | A | 8/1998 | Sagenmüller et al. |
| 5,811,374 | A | 9/1998 | Bertram et al. |
| 5,830,826 | A | 11/1998 | Fischer et al. |
| 5,994,274 | A | 11/1999 | Fischer et al. |
| 6,114,374 | A | 9/2000 | Lieb et al. |
| 6,133,296 | A | 10/2000 | Lieb et al. |
| 6,140,358 | A | 10/2000 | Lieb et al. |
| 6,200,932 | B1 | 3/2001 | Fischer et al. |
| 6,288,102 | B1 | 9/2001 | Hagemann et al. |
| 6,316,486 | B1 | 11/2001 | Lieb et al. |
| 6,358,887 | B1 | 3/2002 | Fischer et al. |
| 6,451,843 | B1 | 9/2002 | Lieb et al. |
| 6,458,965 | B1 | 10/2002 | Lieb et al. |
| 6,472,419 | B1 | 10/2002 | Fischer et al. |
| 6,589,976 | B1 | 7/2003 | Fischer et al. |
| 6,602,823 | B1 | 8/2003 | Röchling et al. |
| 6,608,211 | B1 | 8/2003 | Hagemann et al. |
| 6,645,914 | B1 | 11/2003 | Woznica et al. |
| 6,861,391 | B1 | 3/2005 | Fischer et al. |
| 6,894,005 | B1 | 5/2005 | Maetzke et al. |

(Continued)

FOREIGN PATENT DOCUMENTS

| | | |
|---|---|---|
| CA | 1 162 071 A | 2/1984 |
| CA | 2 671 179 A1 | 6/2008 |

(Continued)

OTHER PUBLICATIONS

Farm Chemicals Handbook '98, Meister Publishing Co., p. B19 (1998).*
Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, Society of Chemical Industry, England (1997).
Ito, M., et al., "Synthesis and Insecticidal Activity of Novel N-Oxydihydropyrrole Derivatives with a Substituted Spirocyclohexyl Group," *Biosci. Biotechnol. Biochem.* 67(6):1230-1238, Japan Society for Bioscience, Biotechnology, and Agrochemistry, Japan (2003).

(Continued)

*Primary Examiner* — John Pak
(74) *Attorney, Agent, or Firm* — Sterne, Kessler, Goldstein & Fox P.L.L.C.

(57) ABSTRACT

The present invention relates to boosting the action of crop protection compositions comprising in particular spiroheterocyclically substituted tetramic acid derivatives of the formula (I) by addition of ammonium or phosphonium salts and optionally penetrants, to the corresponding compositions, to processes for their preparation and to their use in crop protection as insecticides and/or acaricides and/or for preventing unwanted vegetation.

10 Claims, No Drawings

(56) References Cited

U.S. PATENT DOCUMENTS

| | | |
|---|---|---|
| 2003/0171219 A1 | 9/2003 | Lieb et al. |
| 2003/0216260 A1 | 11/2003 | Ruther et al. |
| 2003/0224939 A1 | 12/2003 | Miles |
| 2005/0009880 A1 | 1/2005 | Cottrell et al. |
| 2005/0054535 A1 | 3/2005 | Fischer et al. |
| 2005/0096386 A1 | 5/2005 | Cottrell et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |
| 2008/0167188 A1 | 7/2008 | Fischer et al. |
| 2008/0220973 A1 | 9/2008 | Fischer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0261608 A1 | 10/2010 | Fischer et al. |
| 2010/0311593 A1 | 12/2010 | Fischer et al. |
| 2010/0311777 A1* | 12/2010 | Zambach et al. ............. 514/278 |

FOREIGN PATENT DOCUMENTS

| | | | |
|---|---|---|---|
| CA | 2 695 032 | A1 | 2/2009 |
| CA | 2 700 292 | A1 | 4/2009 |
| CA | 2 718 735 | A1 | 9/2009 |
| DE | 10 2005 059 892 | A1 | 6/2007 |
| EP | 0 262 399 | A2 | 4/1988 |
| EP | 0 453 086 | A2 | 10/1991 |
| GB | 2 266 888 | A | 11/1993 |
| JP | 2000-053670 | A | 2/2000 |
| JP | 2002-205984 | A | 7/2002 |
| WO | WO 92/16108 | A1 | 10/1992 |
| WO | WO 95/17817 | A1 | 7/1995 |
| WO | WO 98/35553 | A1 | 8/1998 |
| WO | WO 03/062244 | A1 | 7/2003 |
| WO | WO 2007/068428 | A2 | 6/2007 |
| WO | WO 2008/067873 | A1 | 6/2008 |
| WO | WO 2008/067910 | A1 | 6/2008 |
| WO | WO 2008/138551 | A2 | 11/2008 |
| WO | WO 2009/049851 | A | 4/2009 |
| WO | WO 2010/052161 | A2 | 5/2010 |
| WO | WO 2010/063670 | A1 | 6/2010 |
| WO | WO 2010/066780 | A1 | 6/2010 |

OTHER PUBLICATIONS

Schmierer, R., and Mildenberger, H., "Cyclisierung von N-Acylalanin- und N-Acylglycinestern" *Liebigs Ann. Chem.* 1095-1098, VCH Verlagsgesellschaft mbH, Germany (1985).

Suzuki, S., et al., "Studies on Antiviral Agents. IV. Biological Activity of Tenuazonic Acid Derivatives," *Chem. Pharm. Bull.* 13(8):1120-1122, Pharmaceutical Society of Japan, Japan (1967).

English language Abstract of Japanese Patent Publication No. 2000-053670, Japanese Patent Office, Patent & Utility Model Gazette DB, Patent Abstracts of Japan (2000).

English language Abstract of Japanese Patent Publication No. 2002-205984, Japanese Patent Office, Patent & Utility Model Gazette DB, Patent Abstracts of Japan (2002).

International Search Report for International Application No. PCT/EP2011/056136, European Patent Office, The Hague, Netherlands, mailed on Jul. 5, 2011.

Uncertified English language translation of German Patent Publication No. DE 10 2005 059 892 A1 published on Jun. 28, 2007.

Uncertified English language translation of WIPO Patent Publication No. WO 2008/067873 A1.

Uncertified English language translation of WIPO Patent Publication No. WO 2008/067910 A1.

Uncertified English language translation of WIPO Patent Publication No. WO 2008/138551 A2.

Uncertified English language machine translation of Schmierer, R., and Mildenberger, H., "Cyclisierung von N-Acylalanin- und N-Acylglycinestern" *Liebigs Ann. Chem.*:1095-1098, VCH Verlagsgesellschaft mbH, Germany (1985).

* cited by examiner

INSECTICIDAL AND/OR HERBICIDAL COMPOSITION HAVING IMPROVED ACTIVITY BASED ON SPIROHETEROCYCLICALLY SUBSTITUTED TETRAMIC ACID DERIVATIVES

The present invention relates to boosting the action of crop protection compositions comprising in particular spiroheterocyclically substituted tetramic acid derivatives by addition of ammonium or phosphonium salts and optionally penetrants, to the corresponding compositions, to processes for their preparation and to their use in crop protection as insecticides and/or acaricides and/or for preventing unwanted vegetation.

For 3-acylpyrrolidine-2,4-diones, pharmaceutical properties have been previously described (S. Suzuki et al. Chem. Pharm. Bull. 15 1120 (1967)). Furthermore, N phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-arylpyrrolidine-2,4-diones) for which, however, no herbicidal, insecticidal or acaricidal action has been disclosed. Known compounds with herbicidal, insecticidal or acaricidal action are unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (WO 10/066, 780, EP-A-377 893 and EP-A-442 077).

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, WO 10/063,378, WO 10/063,670, WO 10/052,161, WO 10/102,758). Moreover, ketal-substituted 1-H-arylpyrrolidine-2,4-diones are known from WO 99/16748 and (spiro)ketal-substituted N-alkoxyalkoxy-substituted arylpyrrolidinediones are known from JP-A-14 205 984 and Ito M. et al., Bioscience, Biotechnology and Biochemistry 67, 1230-1238, (2003). The addition of safeners to ketoenols is also known in principle from WO 03/013249. Moreover, herbicidal compositions comprising ketoenols are known from WO 06/024411.

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. Nos. 4,844,734, 5,462,912, 5,538,937, 03/0224939, 05/0009880, 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost to action by ammonium sulphate, for example, is described by way of example for the herbicides glyphosate, phosphinothricin and for phenyl-substituted cyclic ketoenols (U.S. Pat. No. 6,645,914, EP-A2 0 036 106, e.g. WO 07/068,427). A corresponding boost of action in the case of insecticides has already been described in WO 07/068,428, for example.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the spiroheterocyclically substituted tetramic acid derivatives of the formula (I) can be boosted significantly through the addition of ammonium salts or phosphonium salts to the application solution or through the incorporation of these salts into a formulation comprising spiroheterocyclically substituted tetramic acid derivatives of the formula (I). The present invention therefore provides for the use of ammonium salts or phosphonium salts for boosting the action of crop protection compositions which comprise as active compound herbicidal and/or insecticidal and/or acaricidal spiroheterocyclically substituted tetramic acid derivatives of the formula (I). The invention likewise provides compositions which comprise herbicidal and/or acaricidal and/or insecticidal spiroheterocyclically substituted tetramic acid derivatives of the formula (I) and action-boosting ammonium salts or phosphonium salts, including not only formulated active compounds but also ready-to-use compositions (spray liquors). The invention further provides, finally, for the use of these compositions for controlling harmful insects and/or spider mites and/or unwanted vegetation.

The formula (I) provides a definition of active compounds according to the invention from the class of the spiroheterocyclically substituted tetramic acid derivatives, the activity of which can be enhanced by addition of ammonium salts or phosphonium salts to the formulated or ready-to-use active compound preparations,

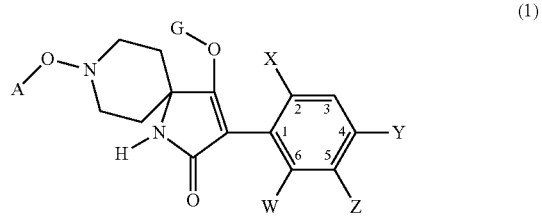

(1)

in which
W represents hydrogen, halogen, alkyl, alkenyl, alkynyl, optionally substituted cycloalkyl which is optionally interrupted by heteroatoms, alkoxy, haloalkyl, haloalkoxy or cyano,
X represents halogen, alkyl, alkenyl, alkynyl, optionally substituted cycloalkyl which is optionally interrupted by heteroatoms, alkoxy, haloalkyl, haloalkoxy or cyano,
Y and Z independently of one another represent hydrogen, alkyl, alkenyl, alkynyl, optionally substituted cycloalkyl which is optionally interrupted by heteroatoms, halogen, alkoxy, haloalkyl or haloalkoxy, A represents hydrogen, in each case optionally substituted alkyl, alkenyl, alkynyl, alkoxyalkyl, phenylalkyl, hetaryalkyl or represents a group G, G represents hydrogen (a) or represents one of the groups

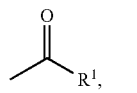
(b)

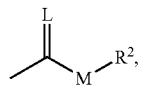
(c)

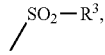
(d)

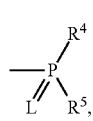
(e)

E or (f)

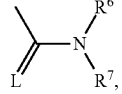
(g)

in which

E represents a metal ion or an ammonium ion,

L represents oxygen or sulphur,

M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the nitrogen atom to which they are attached form a cycle which optionally contains oxygen or sulphur and is optionally substituted.

Depending inter alia on the nature of the substituents, the compounds of the formula (I) may be present as optical isomers or isomer mixtures of varying composition which, if appropriate, may be separated in a customary manner. The present invention provides the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having varying proportions of isomeric compounds.

Including the different meanings (a), (b), (c), (d), (e), (f) and (g) of group G, the following principal structures (I-a) to (I-g) result

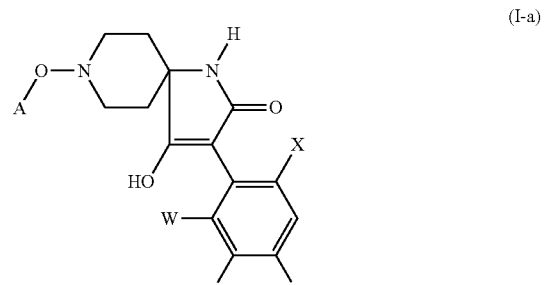
(I-a)

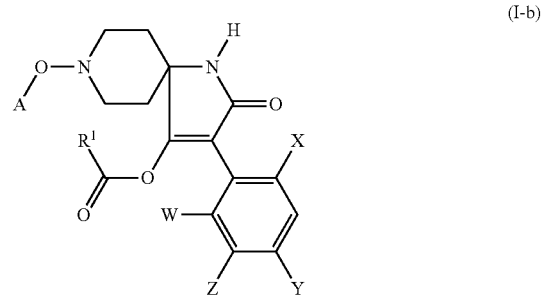
(I-b)

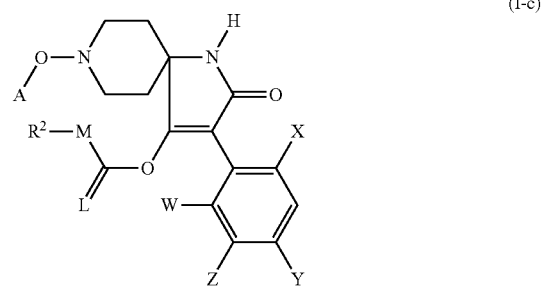
(I-c)

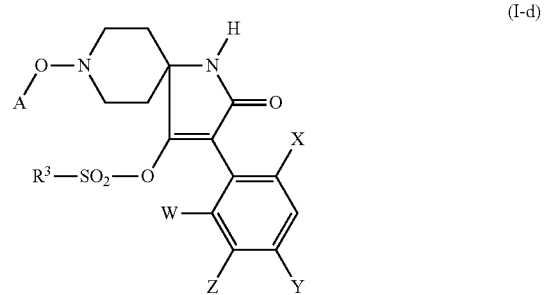
(I-d)

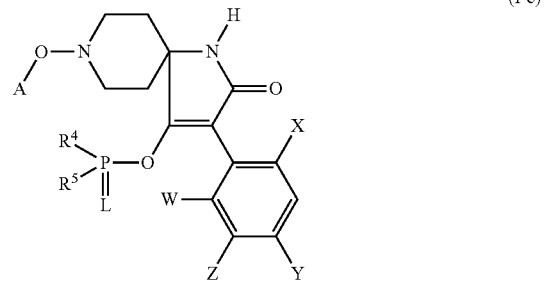
(I-e)

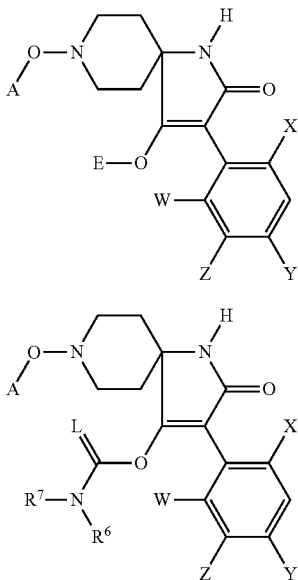

(I-f)

(I-g)

in which

A, E, L, M, W, X, Y, Z, R$^1$, R$^2$, R$^3$, R$^4$, R$^5$, R$^6$ and R$^7$ have the meanings given above.

The compounds of the formula (I) are prepared in particular by the processes described in WO 2009/049851 and in the literature mentioned at the outset.

Formula (I) provides a general definition of the compounds according to the invention. Preferred substituents or ranges of the radicals given in the formulae above and below are illustrated below:

W preferably represents hydrogen, halogen, C$_2$-C$_6$-alkenyl, C$_2$-C$_6$-alkynyl, optionally substituted C$_3$-C$_6$-cycloalkyl which may optionally be interrupted by oxygen or sulphur, C$_1$-C$_6$-alkyl, C$_1$-C$_6$-alkoxy, C$_1$-C$_4$-haloalkyl, C$_1$-C$_4$-haloalkoxy or cyano, X preferably represents halogen, C$_1$-C$_6$-alkyl, C$_2$-C$_6$-alkenyl, C$_2$-C$_6$-alkynyl, optionally substituted C$_3$-C$_6$-cycloalkyl which may optionally be interrupted by oxygen or sulphur, C$_1$-C$_6$-haloalkyl, C$_1$-C$_6$-alkoxy, C$_1$-C$_6$-haloalkoxy or cyano, Y and Z preferably independently of one another represent hydrogen, halogen, C$_1$-C$_6$-alkyl, C$_2$-C$_6$-alkenyl, C$_2$-C$_6$-alkynyl, optionally substituted C$_3$-C$_6$-cycloalkyl which may optionally be interrupted by oxygen or sulphur, C$_1$-C$_6$-alkoxy, C$_1$-C$_6$-haloalkyl, C$_1$-C$_6$-haloalkoxy, A preferably represents hydrogen, C$_1$-C$_6$-alkyl, C$_3$-C$_6$-alkenyl, C$_3$-C$_6$-alkynyl, C$_1$-C$_6$-haloalkyl, C$_1$-C$_6$-cyanoalkyl, C$_1$-C$_4$-alkoxy-C$_1$-C$_4$-alkyl, represents phenyl-(C$_1$-C$_2$)-alkyl or hetaryl-(C$_1$-C$_2$)alkyl, each of which is optionally mono- or polysubstituted by halogen, C$_1$-C$_4$-alkyl, C$_1$-C$_4$-alkoxy, C$_1$-C$_2$-haloalkyl, C$_1$-C$_2$-haloalkoxy or cyano or represents a group G, G preferably represents hydrogen (a) or represents one of the groups

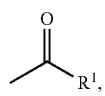

(b)

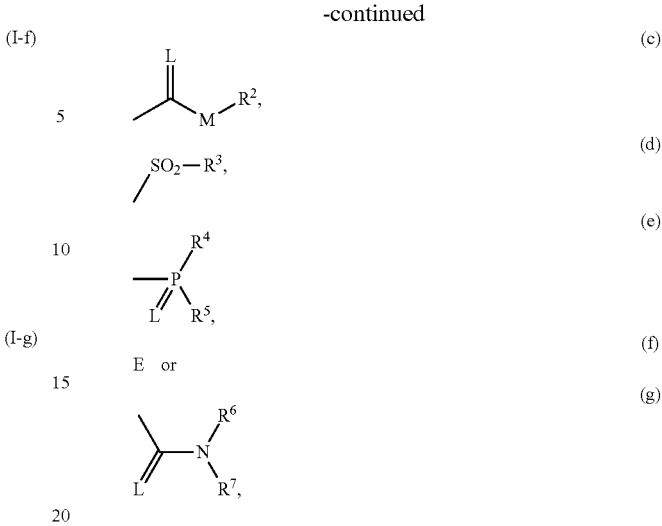

in which

E represents a metal ion or an ammonium ion,

L represents oxygen or sulphur and

M represents oxygen or sulphur,

R$^1$ preferably represents in each case optionally halogen- or cyano-substituted C$_1$-C$_{20}$-alkyl, C$_2$-C$_{20}$-alkenyl, C$_1$-C$_8$-alkoxy-C$_1$-C$_8$-alkyl, C$_1$-C$_8$-alkylthio-C$_1$-C$_8$-alkyl or poly-C$_1$-C$_8$-alkoxy-C$_1$-C$_8$-alkyl or represents optionally halogen-, C$_1$-C$_6$-alkyl- or C$_1$-C$_6$-alkoxy-substituted C$_3$-C$_8$-cycloalkyl in which optionally one or two not directly adjacent methylene groups are replaced by oxygen and/or sulphur, represents optionally halogen-, cyano-, nitro-, C$_1$-C$_6$-alkyl-, C$_1$-C$_6$-alkoxy-, C$_1$-C$_6$-haloalkyl-, C$_1$-C$_6$-haloalkoxy-, C$_1$-C$_6$-alkylthio- or C$_1$-C$_6$-alkylsulphonyl-substituted phenyl, represents optionally halogen-, nitro-, cyano-, C$_1$-C$_6$-alkyl-, C$_1$-C$_6$-alkoxy-, C$_1$-C$_6$-haloalkyl- or C$_1$-C$_6$-haloalkoxy-substituted phenyl-C$_1$-C$_6$-alkyl, represents optionally halogen- or C$_1$-C$_6$-alkyl-substituted 5- or 6-membered hetaryl having one or two heteroatoms from the group consisting of oxygen, sulphur and nitrogen, represents optionally halogen- or C$_1$-C$_6$-alkyl-substituted phenoxy-C$_1$-C$_6$-alkyl or represents optionally halogen-, amino- or C$_1$-C$_6$-alkyl-substituted 5- or 6-membered hetaryloxy-C$_1$-C$_6$-alkyl having one or two heteroatoms from the group consisting of oxygen, sulphur and nitrogen, R$^2$ preferably represents in each case optionally halogen- or cyano-substituted C$_1$-C$_{20}$ alkyl, C$_2$-C$_{20}$-alkenyl, C$_1$-C$_8$-alkoxy-C$_2$-C$_8$-alkyl or poly-C$_1$-C$_8$-alkoxy-C$_2$-C$_8$-alkyl, represents optionally halogen-, C$_1$-C$_6$-alkyl- or C$_1$-C$_6$-alkoxy-substituted C$_3$-C$_8$-cycloalkyl or represents in each case optionally halogen-, cyano-, nitro-, C$_1$-C$_6$-alkyl-, C$_1$-C$_6$-alkoxy-, C$_1$-C$_6$-haloalkyl- or C$_1$-C$_6$-haloalkoxy-substituted phenyl or benzyl, R$^3$ preferably represents optionally halogen-substituted C$_1$-C$_8$-alkyl or in each case optionally halogen-, C$_1$-C$_6$-alkyl-, C$_1$-C$_6$-alkoxy-, C$_1$-C$_4$-haloalkyl-, C$_1$-C$_4$-haloalkoxy-, cyano- or nitro-substituted phenyl or benzyl, R$^4$ and R$^5$ independently of one another preferably represent in each case optionally halogen-substituted C$_1$-C$_8$-alkyl, C$_1$-C$_8$-alkoxy, C$_1$-C$_8$-alkylamino, di-(C$_1$-C$_8$-alkyl)amino, C$_1$-C$_8$-alkylthio or C$_3$-C$_8$-alkenylthio or represent in each case optionally halogen-, nitro-, cyano-, C$_1$-C$_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, fluorine, chlorine, bromine, iodine, $C_1$-$C_4$-alkyl, $C_2$-$C_4$-alkenyl, $C_2$-$C_4$-alkynyl, represents $C_3$-$C_6$-cycloalkyl which is optionally mono- or disubstituted by fluorine, chlorine, methyl, cyclopropyl, methoxy or cyano, represents $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, represents $C_3$-$C_6$-cycloalkyl which is optionally mono- or disubstituted by fluorine, chlorine, methyl, cyclopropyl, methoxy or cyano, represents $C_1$-$C_4$-alkoxy, $C_1$-$C_4$-haloalkyl or $C_1$-$C_4$-haloalkoxy, Y and Z independently of one another particularly preferably represent hydrogen, fluorine, chlorine, bromine, iodine, $C_1$-$C_4$-alkyl, $C_2$-$C_4$-alkenyl, $C_2$-$C_4$-alkynyl, represent $C_3$-$C_6$-cycloalkyl which is optionally mono- or disubstituted by fluorine, chlorine, methyl, cyclopropyl, methoxy or cyano, represent $C_1$-$C_4$-alkoxy, $C_1$-$C_4$-haloalkyl or $C_1$-$C_4$-haloalkoxy, A particularly preferably represents hydrogen, $C_1$-$C_4$-alkyl, $C_1$-$C_4$-haloalkyl, $C_1$-$C_4$-cyanoalkyl, $C_1$-$C_4$-alkoxy-$C_1$-$C_2$-alkyl, represents benzyl or pyridylmethyl, each of which is optionally mono- or disubstituted by fluorine, chlorine, methyl, trifluoromethyl, methoxy or trifluoromethoxy or a group (b), (c) or (g) selected from G, G particularly preferably represents hydrogen (a) or represents one of the groups

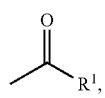
(b)

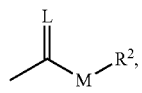
(c)

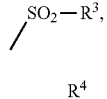
(d)

(e)

(f)

E or

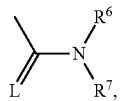
(g)

in which
E represents a metal ion or an ammonium ion,
L represents oxygen or sulphur and
M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$- cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, methoxy or ethoxy (especially preferably hydrogen, methyl or ethyl), X very particularly preferably represents chlorine, bromine, iodine, methyl, ethyl, methoxy, ethoxy, propoxy, cyclopropyl or trifluoromethyl (especially preferably methyl or ethyl), Y and Z very particularly preferably independently of one another represent hydrogen, fluorine, chlorine, bromine, iodine, methyl, ethyl, methoxy, cyclopropyl, trifluoromethyl, trifluoromethoxy or trifluoroethoxy (especially preferably independently of one another hydrogen or methyl), A very particularly preferably represents methyl, ethyl or propyl (especially preferably methyl or ethyl), G very particularly preferably represents hydrogen (a) or represents one of the groups

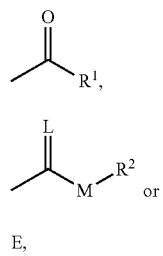

(especially preferably hydrogen (a) or the group (c)),
in which
E represents a metal ion or an ammonium ion,
L represents oxygen or sulphur (especially preferably oxygen) and
M represents oxygen or sulphur (especially preferably oxygen), $R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy,
represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
represents cyclopentyl or cyclohexyl
or represents phenyl or benzyl, each of which is optionally mono- or disubstituted by fluorine, chlorine, cyano, nitro, methyl, ethyl, methoxy, trifluoromethyl or trifluoromethoxy (especially preferably represents $C_1$-$C_{10}$-alkyl).

The general or preferred radical definitions listed above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

With emphasis, G represents hydrogen.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

In addition to the compounds mentioned in the examples, the following compounds of the formula (I) may be specifically mentioned:

TABLE 1

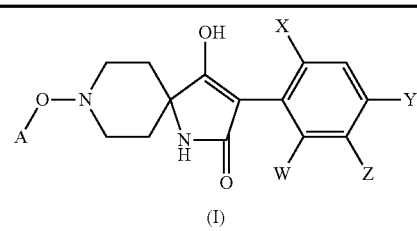

(I)

| A | X | W | Y | Z |
|---|---|---|---|---|
| $CH_3$ | $CH_3$ | H | H | H |
| $CH_3$ | Br | H | H | H |
| $CH_3$ | Cl | H | H | H |
| $CH_3$ | $CF_3$ | H | H | H |
| $CH_3$ | $OCH_3$ | H | H | H |
| $CH_3$ | Br | H | Cl | H |
| $CH_3$ | Cl | H | Br | H |
| $CH_3$ | Cl | H | Cl | H |
| $CH_3$ | Cl | H | $CH_3$ | H |
| $CH_3$ | $CH_3$ | H | Cl | H |
| $CH_3$ | Cl | Cl | H | H |
| $CH_3$ | Cl | $OCH_3$ | H | H |
| $CH_3$ | Cl | $CH_3$ | H | H |
| $CH_3$ | Cl | $OC_2H_5$ | H | H |
| $CH_3$ | $OCH_3$ | $OCH_3$ | H | H |
| $CH_3$ | $CH_3$ | $CH_3$ | H | H |
| $CH_3$ | $C_2H_5$ | $CH_3$ | H | H |
| $CH_3$ | $C_2H_5$ | $C_2H_5$ | H | H |
| $CH_3$ | Br | $CH_3$ | Br | H |

TABLE 1-continued

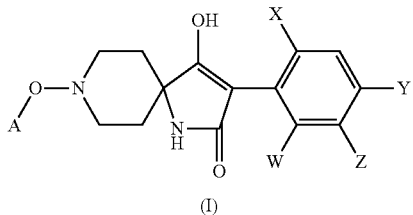

(I)

| A | X | W | Y | Z |
|---|---|---|---|---|
| $CH_3$ | Cl | $CH_3$ | Cl | H |
| $CH_3$ | $CH_3$ | Br | $CH_3$ | H |
| $CH_3$ | $CH_3$ | Cl | $CH_3$ | H |
| $CH_3$ | $OCH_3$ | $CH_3$ | $CH_3$ | H |
| $CH_3$ | $OC_2H_5$ | $CH_3$ | $CH_3$ | H |
| $CH_3$ | $OC_3H_7$ | $CH_3$ | $CH_3$ | H |
| $CH_3$ | $CH_3$ | $CH_3$ | $CH_3$ | H |
| $CH_3$ | Br | Br | $CH_3$ | H |
| $CH_3$ | Cl | Cl | $CH_3$ | H |
| $CH_3$ | $CH_3$ | $CH_3$ | Br | H |
| $CH_3$ | $OCH_3$ | $C_2H_5$ | $CH_3$ | H |
| $CH_3$ | $OC_2H_5$ | $C_2H_5$ | $CH_3$ | H |
| $CH_3$ | $CH_3$ | $CH_3$ | $OCH_3$ | H |
| $CH_3$ | Br | Cl | $CH_3$ | H |
| $CH_3$ | Br | $CH_3$ | Cl | H |
| $CH_3$ | Cl | $CH_3$ | Br | H |
| $CH_3$ | $CH_3$ | $CH_3$ | Cl | H |
| $CH_3$ | $C_2H_5$ | $CH_3$ | $CH_3$ | H |
| $CH_3$ | $C_2H_5$ | $C_2H_5$ | $CH_3$ | H |
| $CH_3$ | $C_2H_5$ | $CH_3$ | $C_2H_5$ | H |
| $CH_3$ | $C_2H_5$ | $C_2H_5$ | $C_2H_5$ | H |
| $CH_3$ | $C_2H_5$ | $CH_3$ | Cl | H |
| $CH_3$ | $C_2H_5$ | $C_2H_5$ | Cl | H |
| $CH_3$ | $C_2H_5$ | $CH_3$ | Br | H |
| $CH_3$ | $C_2H_5$ | $C_2H_5$ | Br | H |
| $CH_3$ | $C_2H_5$ | Cl | $CH_3$ | H |
| $CH_3$ | $C_2H_5$ | Br | $CH_3$ | H |
| $CH_3$ | $C_2H_5$ | Cl | Cl | H |
| $CH_3$ | $C_2H_5$ | Br | Br | H |
| $CH_3$ | $C_2H_5$ | Cl | Br | H |
| $CH_3$ | $C_2H_5$ | Br | Cl | H |
| $CH_3$ | $OCH_3$ | $CH_3$ | Cl | H |
| $CH_3$ | $OCH_3$ | $C_2H_5$ | Cl | H |
| $CH_3$ | $OC_2H_5$ | $CH_3$ | Cl | H |
| $CH_3$ | $OC_2H_5$ | $C_2H_5$ | Cl | H |
| $CH_3$ | Cl | $OCH_3$ | $CH_3$ | H |
| $CH_3$ | Cl | $OC_2H_5$ | $CH_3$ | H |
| $CH_3$ | $CH_3$ | $CH_3$ | Cl | H |
| $CH_3$ | Cl | H | Cl | Cl |
| $CH_3$ | $CH_3$ | H | $CH_3$ | $CH_3$ |
| $CH_3$ | $CH_3$ | H | Cl | $CH_3$ |
| $CH_3$ | Br | H | Cl | $CH_3$ |
| $CH_3$ | Br | H | $CH_3$ | $CH_3$ |
| $CH_3$ | Cl | H | Br | $CH_3$ |
| $CH_3$ | Cl | H | Cl | $CH_3$ |
| $CH_3$ | $CH_3$ | H | Br | $CH_3$ |
| $CH_3$ | Cl | H | $CH_3$ | Cl |
| $CH_3$ | $CH_3$ | H | H | $CH_3$ |
| $CH_3$ | Cl | H | H | $CH_3$ |
| $CH_3$ | Br | H | H | $CH_3$ |
| $CH_3$ | $CH_3$ | H | H | Cl |
| $CH_3$ | $CH_3$ | H | H | Br |
| $CH_3$ | $CH_3$ | $CH_3$ | $CH_3$ | $CH_3$ |
| $CH_3$ | $CH_3$ | $CH_3$ | $CH_3$ | F |
| $CH_3$ | $CH_3$ | $CH_3$ | $CH_3$ | Cl |
| $CH_3$ | $CH_3$ | $CH_3$ | $CH_3$ | Br |
| $CH_3$ | $CH_3$ | $CH_3$ | H | Cl |
| $CH_3$ | $CH_3$ | $CH_3$ | H | Br |
| $CH_3$ | Cl | Cl | H | Br |
| $CH_3$ | I | H | H | H |
| $CH_3$ | I | H | $CH_3$ | H |
| $CH_3$ | I | $CH_3$ | H | H |
| $CH_3$ | I | $C_2H_5$ | H | H |
| $CH_3$ | $CH_3$ | H | H | I |
| $CH_3$ | $CH_3$ | H | $CH_3$ | I |
| $CH_3$ | I | $CH_3$ | $CH_3$ | H |
| $CH_3$ | I | $C_2H_5$ | $CH_3$ | H |

TABLE 1-continued

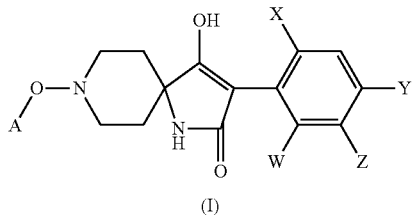

(I)

| A | X | W | Y | Z |
|---|---|---|---|---|
| $CH_3$ | I | $CH_3$ | Cl | H |
| $CH_3$ | I | $C_2H_5$ | Cl | H |
| $CH_3$ | I | Cl | $CH_3$ | H |
| $CH_3$ | I | H | $CH_3$ | $CH_3$ |
| $CH_3$ | $CH_3$ | H | I | H |
| $CH_3$ | $C_2H_5$ | H | I | H |
| $CH_3$ | $CH_3$ | $CH_3$ | I | H |
| $CH_3$ | $C_2H_5$ | $CH_3$ | I | H |
| $CH_3$ | $C_2H_5$ | $C_2H_5$ | I | H |
| $CH_3$ | Cl | $CH_3$ | I | H |
| $CH_3$ | Cl | $C_2H_5$ | I | H |
| $CH_3$ | $CH_3$ | H | I | $CH_3$ |
| $CH_3$ | $CH_3$ | $CH_3$ | H | I |
| $CH_3$ | I | H | H | $CH_3$ |
| $CH_3$ | $C_2H_5$ | H | H | H |
| $CH_3$ | △ | H | H | H |
| $CH_3$ | △ | $CH_3$ | H | H |
| $CH_3$ | △ | H | $CH_3$ | H |
| $CH_3$ | △ | $C_2H_5$ | H | H |
| $CH_3$ | △ | $CH_3$ | $CH_3$ | H |
| $CH_3$ | △ | $C_2H_5$ | $CH_3$ | H |
| $CH_3$ | △ | $CH_3$ | Cl | H |
| $CH_3$ | △ | $C_2H_5$ | Cl | H |
| $CH_3$ | △ | Cl | $CH_3$ | H |
| $CH_3$ | $CH_3$ | H | △ | H |
| $CH_3$ | $C_2H_5$ | H | △ | H |
| $CH_3$ | $CH_3$ | $CH_3$ | △ | H |
| $CH_3$ | $C_2H_5$ | $CH_3$ | △ | H |
| $CH_3$ | $C_2H_5$ | $C_2H_5$ | △ | H |
| $CH_3$ | Cl | $CH_3$ | △ | H |
| $CH_3$ | Cl | $C_2H_5$ | △ | H |
| $CH_3$ | $CH_3$ | H | $O-CH_2-CF_3$ | H |

TABLE 1-continued

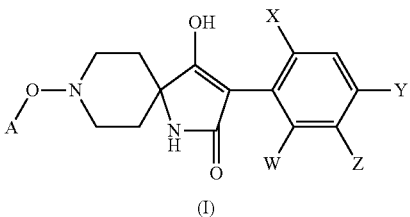

(I)

| A | X | W | Y | Z |
|---|---|---|---|---|
| CH$_3$ | CH$_3$ | CH$_3$ | O—CH$_2$—CF$_3$ | H |
| CH$_3$ | CH$_3$ | H | H | O—CH$_2$—CF$_3$ |
| CH$_3$ | CH$_3$ | CH$_3$ | H | O—CH$_2$—CF$_3$ |
| CH$_3$ | C$_2$H$_5$ | H | O—CH$_2$—CF$_3$ | H |
| CH$_3$ | C$_2$H$_5$ | CH$_3$ | O—CH$_2$—CF$_3$ | H |
| CH$_3$ | C$_2$H$_5$ | C$_2$H$_5$ | O—CH$_2$—CF$_3$ | H |
| CH$_3$ | C$_2$H$_5$ | CH$_3$ | H | O—CH$_2$—CF$_3$ |
| CH$_3$ | C$_2$H$_5$ | C$_2$H$_5$ | H | O—CH$_2$—CF$_3$ |

Table 2 W, X, Y and Z as stated in Table 1
A=C$_2$H$_5$
Table 3 W, X, Y and Z as stated in Table 1
A=C$_3$H$_7$ The active compounds can be used in the compositions according to the invention in a broad concentration range. The concentration of the active compounds in the formulation is typically 0.1%-50% by weight.

The formula (III') provides a definition of the ammonium salts and phosphonium salts which, according to the invention, boost the activity of crop protection compositions comprising compounds of the formula (I)

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26}$, $R^{27}$, $R^{28}$ and $R^{29}$ very particularly preferably represent hydrogen,
n represents 1, 2, 3 or 4,
n preferably represents 1 or 2,
$R^{30}$ represents an organic or inorganic anion,
$R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, monohydrogenphosphate, dihydrogenphosphate, sulphate, nitrate, thiosulphate, thiocyanate, oxalate or formate,
$R^{30}$ very particularly preferably represents sulphate.

The ammonium salts and phosphonium salts of the formula (III') can be used in a broad concentration range to boost the activity of crop protection compositions comprising spiroheterocyclically substituted tetramic acid derivatives of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In a preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or herbicidal spiroheterocyclically substituted tetramic acid derivatives of the formula (I) as active compound. The invention likewise provides compositions which comprise herbicidal and/or acaricidal and/or insecticidal spiroheterocyclically substituted tetramic acid derivatives of the formula (I), penetrants and ammonium salts and/or phosphonium salts, including specifically not only formulated active compounds but also ready-to-use compositions (spray liquors). The invention additionally provides, finally, for the use of these compositions for controlling harmful insects, spider mites and/or vegetation.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or represents mixtures of ethylene oxide and propylene oxide radicals or butylene oxide radicals, and
v represents a number from 2 to 30.

A preferred group of penetrants are alkanol alkoxylates of the formula

in which
R has the meaning given above,
R' has the meaning given above,
EO represents —CH$_2$—CH$_2$—O—, and
n represents a number from 2 to 20.

A further preferred group of penetrants are alkanol alkoxylates of the formula

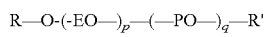  (IV'-b)

in which
R has the meaning given above,
R' has the meaning given above,
EO represents —CH$_2$—CH$_2$—O—,
PO represents

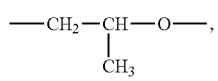

p represents a number from 1 to 10, and
q represents a number from 1 to 10.

A further preferred group of penetrants are alkanol alkoxylates of the formula

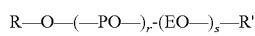  (IV''-c)

in which
R has the meaning given above,
R' has the meaning given above,
EO represents —CH$_2$—CH$_2$—O—,
PO represents

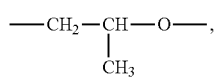

r represents a number from 1 to 10, and
s represents a number from 1 to 10.

A further preferred group of penetrants are alkanol alkoxylates of the formula

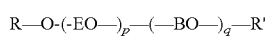  (IV'-d)

in which
R and R' have the meanings given above,
EO represents —CH$_2$—CH$_2$—O—,
BO represents

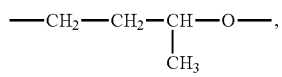

p represents a number from 1 to 10 and
q represents a number from 1 to 10.

A further preferred group of penetrants are alkanol alkoxylates of the formula

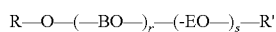  (IV'-e)

in which
R and R' have the meanings given above,
BO is

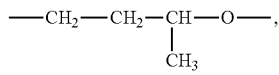

EO is —CH$_2$—CH$_2$—O—,
r represents a number from 1 to 10 and
s represents a number from 1 to 10.

A further preferred group of penetrants are alkanol alkoxylates of the formula

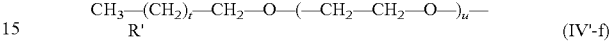  (IV'-f)

in which
R' has the meaning given above,
t represents a number from 8 to 13,
u represents a number from 6 to 17.

In the formulae indicated above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

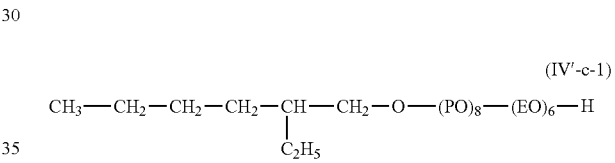  (IV'-c-1)

in which
EO represents —CH$_2$—CH$_2$—O—,
PO represents

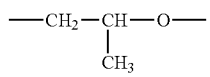

and
the numbers 8 and 6 represent average values.

As an example of an alkanol alkoxylate of the formula (IV'-d) mention may be made of the formula

  (IV'-d-1)

in which
EO represents —CH$_2$—CH$_2$—O—,
BO represents

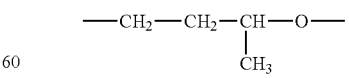

and the numbers 10, 6 and 2 represent average values.

Particularly preferred alkanol alkoxylates of the formula (IV'-f) are compounds of this formula in which
t represents a number from 9 to 12 and
u represents a number from 7 to 9.

Mention may be made with very particular preference of alkanol alkoxylate of the formula (IV'-f-1)

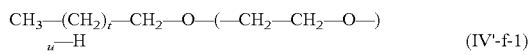  (IV'-f-1)

in which
t represents the average value 10.5 and
u represents the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially (for example under the tradenames Genapol, Marlipal, Lutensol, Reflex) or can be prepared by known methods (cf. WO 98/37 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters. Emphasis is given to rapeseed oil methyl ester.

The concentration of penetrant in the compositions of the invention can be varied within a wide range. In the case of a formulated crop protection composition it is in general 1% to 95%, preferably 1% to 55%, particularly preferably 15%-40%, by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably, mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and also of polyoxyalkyleneamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colourants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Combinations of active compound, salt and penetrant which are emphasized according to the invention are listed in the table below. Here, "penetrant as per test" means that any compound that acts as a penetrant in the cuticle penetration test (Baur et al., 1997, Pesticide Science 51, 131-152) is suitable.

| # | Active compound | Salt | Penetrant |
|---|---|---|---|
| 1 | (I-a-1) | ammonium sulphate | as per test |
| 2 | (I-a-1) | ammonium lactate | as per test |
| 3 | (I-a-1) | ammonium nitrate | as per test |
| 4 | (I-a-1) | ammonium thiosulphate | as per test |
| 5 | (I-a-1) | ammonium thiocyanate | as per test |
| 6 | (I-a-1) | ammonium citrate | as per test |
| 7 | (I-a-1) | ammonium oxalate | as per test |
| 8 | (I-a-1) | ammonium formate | as per test |
| 9 | (I-a-1) | ammonium hydrogenphosphate | as per test |
| 10 | (I-a-1) | ammonium dihydrogenphosphate | as per test |
| 11 | (I-a-1) | ammonium carbonate | as per test |
| 12 | (I-a-1) | ammonium benzoate | as per test |
| 13 | (I-a-1) | ammonium sulphite | as per test |
| 14 | (I-a-1) | ammonium benzoate | as per test |
| 15 | (I-a-1) | ammonium hydrogenoxalate | as per test |
| 16 | (I-a-1) | ammonium hydrogencitrate | as per test |
| 17 | (I-a-1) | ammonium acetate | as per test |
| 18 | (I-a-1) | tetramethylammonium sulphate | as per test |
| 19 | (I-a-1) | tetramethylammonium lactate | as per test |
| 20 | (I-a-1) | tetramethylammonium nitrate | as per test |
| 21 | (I-a-1) | tetramethylammonium thiosulphate | as per test |
| 22 | (I-a-1) | tetramethylammonium thiocyanate | as per test |
| 23 | (I-a-1) | tetramethylammonium citrate | as per test |
| 24 | (I-a-1) | tetramethylammonium oxalate | as per test |
| 25 | (I-a-1) | tetramethylammonium formate | as per test |

| # | Active compound | Salt | Penetrant |
|---|---|---|---|
| 26 | (I-a-1) | tetramethylammonium hydrogenphosphate | as per test |
| 27 | (I-a-1) | tetramethylammonium dihydrogenphosphate | as per test |
| 28 | (I-a-1) | tetraethylammonium sulphate | as per test |
| 29 | (I-a-1) | tetraethylammonium lactate | as per test |
| 30 | (I-a-1) | tetraethylammonium nitrate | as per test |
| 31 | (I-a-1) | tetraethylammonium thiosulphate | as per test |
| 32 | (I-a-1) | tetraethylammonium thiocyanate | as per test |
| 33 | (I-a-1) | tetraethylammonium citrate | as per test |
| 34 | (I-a-1) | tetraethylammonium oxalate | as per test |
| 35 | (I-a-1) | tetraethylammonium formate | as per test |
| 36 | (I-a-1) | tetraethylammonium hydrogenphosphate | as per test |
| 37 | (I-a-1) | tetraethylammonium dihydrogenphosphate | as per test |
| 38 | (I-a-2) | ammonium sulphate | as per test |
| 39 | (I-a-2) | ammonium lactate | as per test |
| 40 | (I-a-2) | ammonium nitrate | as per test |
| 41 | (I-a-2) | ammonium thiosulphate | as per test |
| 42 | (I-a-2) | ammonium thiocyanate | as per test |
| 43 | (I-a-2) | ammonium citrate | as per test |
| 44 | (I-a-2) | ammonium oxalate | as per test |
| 45 | (I-a-2) | ammonium formate | as per test |
| 46 | (I-a-2) | ammonium hydrogenphosphate | as per test |
| 47 | (I-a-2) | ammonium dihydrogenphosphate | as per test |
| 48 | (I-a-2) | ammonium carbonate | as per test |
| 49 | (I-a-2) | ammonium benzoate | as per test |
| 50 | (I-a-2) | ammonium sulphite | as per test |
| 51 | (I-a-2) | ammonium benzoate | as per test |
| 52 | (I-a-2) | ammonium hydrogenoxalate | as per test |
| 53 | (I-a-2) | ammonium hydrogencitrate | as per test |
| 54 | (I-a-2) | ammonium acetate | as per test |
| 55 | (I-a-2) | tetramethylammonium sulphate | as per test |
| 56 | (I-a-2) | tetramethylammonium lactate | as per test |
| 57 | (I-a-2) | tetramethylammonium nitrate | as per test |
| 58 | (I-a-2) | tetramethylammonium thiosulphate | as per test |
| 59 | (I-a-2) | tetramethylammonium thiocyanate | as per test |
| 60 | (I-a-2) | tetramethylammonium citrate | as per test |
| 61 | (I-a-2) | tetramethylammonium oxalate | as per test |
| 62 | (I-a-2) | tetramethylammonium formate | as per test |
| 63 | (I-a-2) | tetramethylammonium hydrogenphosphate | as per test |
| 64 | (I-a-2) | tetramethylammonium dihydrogenphosphate | as per test |
| 65 | (I-a-2) | tetraethylammonium sulphate | as per test |
| 66 | (I-a-2) | tetraethylammonium lactate | as per test |
| 67 | (I-a-2) | tetraethylammonium nitrate | as per test |
| 68 | (I-a-2) | tetraethylammonium thiosulphate | as per test |
| 69 | (I-a-2) | tetraethylammonium thiocyanate | as per test |
| 70 | (I-a-2) | tetraethylammonium citrate | as per test |
| 71 | (I-a-2) | tetraethylammonium oxalate | as per test |
| 72 | (I-a-2) | tetraethylammonium formate | as per test |
| 73 | (I-a-2) | tetraethylammonium hydrogenphosphate | as per test |
| 74 | (I-a-2) | tetraethylammonium dihydrogenphosphate | as per test |
| 75 | (I-c-1) | ammonium sulphate | as per test |
| 76 | (I-c-1) | ammonium lactate | as per test |
| 77 | (I-c-1) | ammonium nitrate | as per test |
| 78 | (I-c-1) | ammonium thiosulphate | as per test |
| 79 | (I-c-1) | ammonium thiocyanate | as per test |
| 80 | (I-c-1) | ammonium citrate | as per test |
| 81 | (I-c-1) | ammonium oxalate | as per test |
| 82 | (I-c-1) | ammonium formate | as per test |
| 83 | (I-c-1) | ammonium hydrogenphosphate | as per test |
| 84 | (I-c-1) | ammonium dihydrogenphosphate | as per test |
| 85 | (I-c-1) | ammonium carbonate | as per test |
| 86 | (I-c-1) | ammonium benzoate | as per test |
| 87 | (I-c-1) | ammonium sulphite | as per test |
| 88 | (I-c-1) | ammonium benzoate | as per test |
| 89 | (I-c-1) | ammonium hydrogenoxalate | as per test |
| 90 | (I-c-1) | ammonium hydrogencitrate | as per test |
| 91 | (I-c-1) | ammonium acetate | as per test |
| 92 | (I-c-1) | tetramethylammonium sulphate | as per test |
| 93 | (I-c-1) | tetramethylammonium lactate | as per test |
| 94 | (I-c-1) | tetramethylammonium nitrate | as per test |
| 95 | (I-c-1) | tetramethylammonium thiosulphate | as per test |
| 96 | (I-c-1) | tetramethylammonium thiocyanate | as per test |
| 97 | (I-c-1) | tetramethylammonium citrate | as per test |
| 98 | (I-c-1) | tetramethylammonium oxalate | as per test |
| 99 | (I-c-1) | tetramethylammonium formate | as per test |
| 100 | (I-c-1) | tetramethylammonium hydrogenphosphate | as per test |
| 101 | (I-c-1) | tetramethylammonium dihydrogenphosphate | as per test |

-continued

| # | Active compound | Salt | Penetrant |
|---|---|---|---|
| 102 | (I-c-1) | tetraethylammonium sulphate | as per test |
| 103 | (I-c-1) | tetraethylammonium lactate | as per test |
| 104 | (I-c-1) | tetraethylammonium nitrate | as per test |
| 105 | (I-c-1) | tetraethylammonium thiosulphate | as per test |
| 106 | (I-c-1) | tetraethylammonium thiocyanate | as per test |
| 107 | (I-c-1) | tetraethylammonium citrate | as per test |
| 108 | (I-c-1) | tetraethylammonium oxalate | as per test |
| 109 | (I-c-1) | tetraethylammonium formate | as per test |
| 110 | (I-c-1) | tetraethylammonium hydrogenphosphate | as per test |
| 111 | (I-c-1) | tetraethylammonium dihydrogenphosphate | as per test |
| 112 | (I-a-3) | ammonium sulphate | as per test |
| 113 | (I-a-3) | ammonium lactate | as per test |
| 114 | (I-a-3) | ammonium nitrate | as per test |
| 115 | (I-a-3) | ammonium thiosulphate | as per test |
| 116 | (I-a-3) | ammonium thiocyanate | as per test |
| 117 | (I-a-3) | ammonium citrate | as per test |
| 118 | (I-a-3) | ammonium oxalate | as per test |
| 119 | (I-a-3) | ammonium formate | as per test |
| 120 | (I-a-3) | ammonium hydrogenphosphate | as per test |
| 121 | (I-a-3) | ammonium dihydrogenphosphate | as per test |
| 122 | (I-a-3) | ammonium carbonate | as per test |
| 123 | (I-a-3) | ammonium benzoate | as per test |
| 124 | (I-a-3) | ammonium sulphite | as per test |
| 125 | (I-a-3) | ammonium benzoate | as per test |
| 126 | (I-a-3) | ammonium hydrogenoxalate | as per test |
| 127 | (I-a-3) | ammonium hydrogencitrate | as per test |
| 128 | (I-a-3) | ammonium acetate | as per test |
| 129 | (I-a-3) | tetramethylammonium sulphate | as per test |
| 130 | (I-a-3) | tetramethylammonium lactate | as per test |
| 131 | (I-a-3) | tetramethylammonium nitrate | as per test |
| 132 | (I-a-3) | tetramethylammonium thiosulphate | as per test |
| 133 | (I-a-3) | tetramethylammonium thiocyanate | as per test |
| 134 | (I-a-3) | tetramethylammonium citrate | as per test |
| 135 | (I-a-3) | tetramethylammonium oxalate | as per test |
| 136 | (I-a-3) | tetramethylammonium formate | as per test |
| 137 | (I-a-3) | tetramethylammonium hydrogenphosphate | as per test |
| 138 | (I-a-3) | tetramethylammonium dihydrogenphosphate | as per test |
| 139 | (I-a-3) | tetraethylammonium sulphate | as per test |
| 140 | (I-a-3) | tetraethylammonium lactate | as per test |
| 141 | (I-a-3) | tetraethylammonium nitrate | as per test |
| 142 | (I-a-3) | tetraethylammonium thiosulphate | as per test |
| 143 | (I-a-3) | tetraethylammonium thiocyanate | as per test |
| 144 | (I-a-3) | tetraethylammonium citrate | as per test |
| 145 | (I-a-3) | tetraethylammonium oxalate | as per test |
| 146 | (I-a-3) | tetraethylammonium formate | as per test |
| 147 | (I-a-3) | tetraethylammonium hydrogenphosphate | as per test |
| 148 | (I-a-3) | tetraethylammonium dihydrogenphosphate | as per test |
| 149 | (I-a-4) | ammonium sulphate | as per test |
| 150 | (I-a-4) | ammonium lactate | as per test |
| 151 | (I-a-4) | ammonium nitrate | as per test |
| 152 | (I-a-4) | ammonium thiosulphate | as per test |
| 153 | (I-a-4) | ammonium thiocyanate | as per test |
| 154 | (I-a-4) | ammonium citrate | as per test |
| 155 | (I-a-4) | ammonium oxalate | as per test |
| 156 | (I-a-4) | ammonium formate | as per test |
| 157 | (I-a-4) | ammonium hydrogenphosphate | as per test |
| 158 | (I-a-4) | ammonium dihydrogenphosphate | as per test |
| 159 | (I-a-4) | ammonium carbonate | as per test |
| 160 | (I-a-4) | ammonium benzoate | as per test |
| 161 | (I-a-4) | ammonium sulphite | as per test |
| 162 | (I-a-4) | ammonium benzoate | as per test |
| 163 | (I-a-4) | ammonium hydrogenoxalate | as per test |
| 164 | (I-a-4) | ammonium hydrogencitrate | as per test |
| 165 | (I-a-4) | ammonium acetate | as per test |
| 166 | (I-a-4) | tetramethylammonium sulphate | as per test |
| 167 | (I-a-4) | tetramethylammonium lactate | as per test |
| 168 | (I-a-4) | tetramethylammonium nitrate | as per test |
| 169 | (I-a-4) | tetramethylammonium thiosulphate | as per test |
| 170 | (I-a-4) | tetramethylammonium thiocyanate | as per test |
| 171 | (I-a-4) | tetramethylammonium citrate | as per test |
| 172 | (I-a-4) | tetramethylammonium oxalate | as per test |
| 173 | (I-a-4) | tetramethylammonium formate | as per test |
| 174 | (I-a-4) | tetramethylammonium hydrogenphosphate | as per test |
| 175 | (I-a-4) | tetramethylammonium dihydrogenphosphate | as per test |
| 176 | (I-a-4) | tetraethylammonium sulphate | as per test |
| 177 | (I-a-4) | tetraethylammonium lactate | as per test |

-continued

| #   | Active compound | Salt                                      | Penetrant   |
|-----|-----------------|-------------------------------------------|-------------|
| 178 | (I-a-4)         | tetraethylammonium nitrate                | as per test |
| 179 | (I-a-4)         | tetraethylammonium thiosulphate           | as per test |
| 180 | (I-a-4)         | tetraethylammonium thiocyanate            | as per test |
| 181 | (I-a-4)         | tetraethylammonium citrate                | as per test |
| 182 | (I-a-4)         | tetraethylammonium oxalate                | as per test |
| 183 | (I-a-4)         | tetraethylammonium formate                | as per test |
| 184 | (I-a-4)         | tetraethylammonium hydrogenphosphate      | as per test |
| 185 | (I-a-4)         | tetraethylammonium dihydrogenphosphate    | as per test |

The examples below serve to illustrate the invention and are not to be understood as limiting the invention in any way.

USE EXAMPLES

Example 1

Activity Boost Through Ammonium/Phosphonium Salts in Combination with Penetrants

*Myzus persicae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration. For application with ammonium salts or phosphonium salts and penetration promoters (rapeseed oil methyl ester 500 EW) these are in each case added in a concentration of 1000 ppm to the spray liquor.

Bell pepper plants (*Capsicum annuum*) heavily infested by the green peach aphid (*Myzus persicae*) are sprayed to runoff point with the preparation of active compound at the desired concentration.

After the desired period of time, the kill in % is determined. 100% means that all animals have been killed; 0% means that none of the animals have been killed.

TABLE

| Active compound | Concentration (ppm) | Kill (%) after 6 d | +AS 1000 ppm | +RME 1000 ppm | +AS + RME per 1000 ppm |
|---|---|---|---|---|---|
| I-a-1 | 20  | 0 | 0  | 0  | 60 |
| I-a-2 | 4   | 0 | 55 | 60 | 95 |
|       | 0.8 | 0 | 0  | 0  | 90 |
| I-c-1 | 20  | 0 | 0  | 20 | 98 |

RME = rapeseed oil methyl ester
AS = ammonium sulphate

Example 2

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. For application with ammonium salts or phosphonium salts and penetration promoters (rapeseed oil methyl ester 500 EW) these are in each case added in a concentration of 1000 ppm of a.i. to the spray liquor.

Cotton plants (*Gossypium hirsutum*) which are heavily infested by the cotton aphid (*Aphis gossypii*) are sprayed to runoff point with the preparation of active compound at the desired concentration.

After the desired period of time, the kill in % is determined. 100% means that all aphids have been killed; 0% means that none of the aphids have been killed.

TABLE

| Active compound | Concentration (ppm) | Kill (%) after 6 d | +AS 1000 ppm | +RME 1000 ppm | +AS + RME per 1000 ppm |
|---|---|---|---|---|---|
| I-a-2 | 20 | 0 | 85 | 95 | 95 |
|       | 4  | 0 | 0  | 40 | 90 |
| I-c-1 | 20 | 0 | 0  | 80 | 90 |

Example 3

Herbicidal Post-Emergence Action

Seeds of monocotyledonous weed plants are placed in sandy loam in wood fibre pots, covered with soil and cultivated in a greenhouse under good growth conditions. 3-4 weeks after sowing, the test plants are treated at the two- to three-leaf stage. The test compound, formulated as a wettable powder (WP), is then, at various dosages with a water application rate of 300 l/ha (converted), with the stated adjuvants added, sprayed onto the green parts of the plants. After the test plants have been kept in the greenhouse under optimum growth conditions for about 4 weeks, the effect of the preparations is rated visually in comparison to untreated controls (herbicidal effect in percent: 100% effect=the plants have died, 0% effect=like control plants).

| Ex. I-a-3 Application rate 6.25 g of a.i./ha | a.i. [1] | a.i. + AS [1] | a.i. + GE [1] | a.i. + AS + GE [1] |
|---|---|---|---|---|
| ALOMY          | 0  | 0  | 70 | 90 |
| ALOMY (Peldon) | 0  | 0  | 20 | 60 |
| LOLMU          | 20 | 40 | 50 | 80 |
| LOLRI          | 0  | 0  | 20 | 60 |

[1] observed values in (%), 28 days after application
+AS = with ammonium sulphate (2 kg/ha);
+GE = Genapol LRO (1 l/ha)
ALOMY = Blackgrass (not resistant)
ALOMY (Peldon) = Blackgrass (resistant)
LOLMU = Italian Ryegrass
LOLRI = Annual Ryegrass (resistant)

Example 4

Increase of Penetration into the Plant by Ammonium or Phosphonium Salts and Synergistic Increase of Penetration into the Plant by Ammonium/Phosphonium Salts in Combination with Penetrants In this test, the penetration of active compounds through enzymatically isolated cuticles of apple tree leaves is measured.

Use is made of leaves which, when fully developed, are cut from apple trees of the cultivar Golden Delicious. The cuticles are isolated by initially filling leaf discs punched out and stained with dye on the underside by vacuum infiltration with a pectinase solution (0.2 to 2% strength) buffered to a pH between 3 and 4, then adding sodium azide and allowing the leaf discs treated in this manner to stand until the original leaf structure has dissolved and the noncellular cuticles have detached.

Only the cuticles, free from hairs and stoma, of the upper sides of the leaves are then used. They are washed repeatedly alternating with water and a buffer solution of pH 7. The clean cuticles obtained are then mounted on Teflon plates and smoothed and dried with a gentle stream of air.

In the next step, the cuticle membranes obtained in this manner are placed into stainless steel diffusion cells (=transport chambers) for membrane transport studies. To this end, the cuticles are placed with a pincette into the centre of the edges, coated with silicone fat, of the diffusion cells and closed with a ring, which is also treated with fat. The arrangement is chosen such that the morphological outside of the cuticles is facing outwards, i.e. exposed to air, whereas the original inside is facing the interior of the diffusion cell.

The diffusion cells are filled with a 30% strength ethylene glycol/water solution. To determine the penetration, in each case 10 µl of the spray liquor of the composition below are applied to the outside of the cuticles. The spray liquor is prepared using local tap water of medium hardness.

After the application of the spray liquors, the water is allowed to evaporate and the chambers are inverted and placed into thermostatic tubs in which temperature and atmospheric humidity over the cuticles can be adjusted using a gentle stream of air onto the cuticles with the spray coating (20° C., 60% rh). At regular intervals, an autosampler takes aliquots and the active compound content is determined by HPLC.

The test results are shown in the table below. The stated numbers are average values of 8 to 10 measurements. It is clearly evident that even the ammonium salts on their own improve the penetration markedly, and that, together with RME, a superadditive (synergistic) effect is present.

| Active compound | Penetration after 24 h/% | | | |
|---|---|---|---|---|
| Example I-a-1 0.1 g/l 500 ppm in DMF/ emulsifier W 7:1 (w/w) | EC | EC + AS (1 g/l) | EC + RME (1 g/l) | EC + RME (1 g/l) + AS (1 g/l) |
| | 0.7 | 17 | 1.7 | 21 |
| | EC | EC + DAHP | EC + RME | EC + RME |
| | | (1 g/l) | (1 g/l) | (1 g/l) + DAHP (1 g/l) |
| | 0.7 | 15 | 1.7 | 28 |

RME = rapeseed oil methyl ester (use formulated as 500 EW, concentration stated in g of active compound/l)
AS = ammonium sulphate
DAHP = diammonium hydrogenphosphate
EC = emulsifiable concentrate

Example 5

Increase of Penetration into the Plant by Ammonium or Phosphonium Salts and Synergistic Increase of Penetration into the Plant by Ammonium/Phosphonium Salts in Combination with Penetrants In this test, the penetration of active compounds through enzymatically isolated cuticles of apple tree leaves is measured.

Use is made of leaves which, when fully developed, are cut from apple trees of the cultivar Golden Delicious. The cuticles are isolated by initially filling leaf discs punched out and stained with dye on the underside by vacuum infiltration with a pectinase solution (0.2 to 2% strength) buffered to a pH between 3 and 4, then adding sodium azide and allowing the leaf discs treated in this manner to stand until the original leaf structure has dissolved and the noncellular cuticles have detached.

Only the cuticles, free from hairs and stoma, of the upper sides of the leaves are then used. They are washed repeatedly alternating with water and a buffer solution of pH 7. The clean cuticles obtained are then mounted on Teflon plates and smoothed and dried with a gentle stream of air.

In the next step, the cuticle membranes obtained in this manner are placed into stainless steel diffusion cells (=transport chambers) for membrane transport studies. To this end, the cuticles are placed with a pincette into the centre of the edges, coated with silicone fat, of the diffusion cells and closed with a ring, which is also treated with fat. The arrangement is chosen such that the morphological outside of the cuticles is facing outwards, i.e. exposed to air, whereas the original inside is facing the interior of the diffusion cell.

The diffusion cells are filled with a 30% strength ethylene glycol/water solution. To determine the penetration, in each case 10 µl of the spray liquor of the composition below are applied to the outside of the cuticles. The spray liquor is prepared using local tap water of medium hardness.

After the application of the spray liquors, the water is allowed to evaporate and the chambers are inverted and placed into thermostatic tubs in which temperature and atmospheric humidity over the cuticles can be adjusted using a gentle stream of air onto the cuticles with the spray coating (35° C., 60% rh). At regular intervals, an autosampler takes aliquots and the active compound content is determined by HPLC.

The test results are shown in the table below. The stated numbers are average values of 8 to 10 measurements. It is clearly evident that even the ammonium salts on their own improve the penetration markedly, and that, together with RME, a superadditive (synergistic) effect is present.

| Active compound | | Penetration after 48 h/% | | |
|---|---|---|---|---|
| | EC | EC + AS (0.7 g/l) | EC + RME (1 g/l) | EC + RME (1 g/l) + AS (0.7 g/l) |
| Example I-a-3 0.2 g/l 500 ppm in DMF/ emulsifier W 7:1 (w/w) | 1 | 9 | 9 | 33 |

RME = rapeseed oil methyl ester (use formulated as 500 EW, concentration stated in g of active compound/l)
AS = ammonium sulphate
EC = emulsifiable concentrate

| Active compound | | Penetration after 48 h/% | | |
|---|---|---|---|---|
| | EC | EC + AS (0.7 g/l) | EC + RME (1 g/l) | EC + RME (1 g/l) + AS (0.7 g/l) |
| Example I-a-4 0.2 g/l 500 ppm in DMF/ emulsifier W 7:1 (w/w) | 0 | 3 | 6 | 17 |

RME = rapeseed oil methyl ester (use formulated as 500 EW, concentration stated in g of active compound/l)
AS = ammonium sulphate
EC = emulsifiable concentrate The following examples are tested

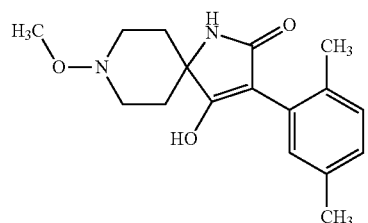

I-a-1

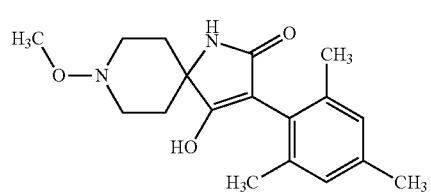

I-a-2

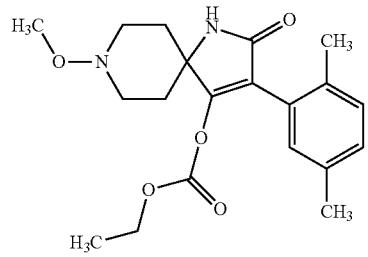

I-c-1

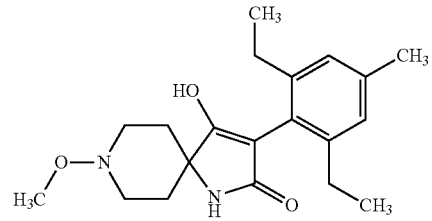

I-a-3

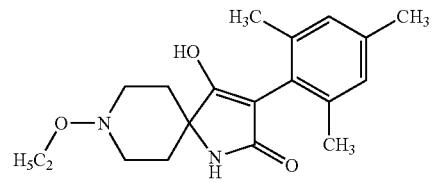

I-a-4

The invention claimed is:

1. A composition comprising a compound of formula (I) and a salt of formula (III'):

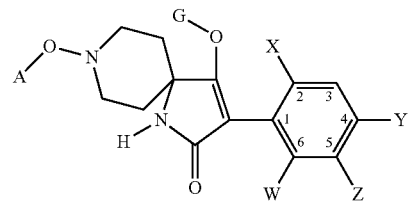

(I)

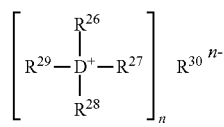

(III')

wherein in formula (I),

W represents hydrogen, chlorine, bromine, methyl, ethyl, methoxy or ethoxy,

X represents chlorine, bromine, iodine, methyl, ethyl, methoxy, ethoxy, propoxy, cyclopropyl or trifluoromethyl, Y and Z independently of one another represent hydrogen, fluorine, chlorine, bromine, iodine, methyl, ethyl, methoxy, cyclopropyl, trifluoromethyl, trifluoromethoxy or trifluoroethoxy, A represents methyl, ethyl or propyl, G represents hydrogen (a), or represents

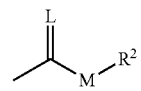

(c)

in which

L represents oxygen,

M represents oxygen, $R^2$ represents $C_1$-$C_{10}$-alkyl, $C_2$-$C_{10}$-alkenyl or $C$ -$C_4$- alkoxy-$C_2$-$C_4$-alkyl, each of which is optionally mono- to trisubstituted by fluorine or chlorine, or represents cyclopentyl or cyclohexyl, or represents phenyl or benzyl, each of which is optionally mono- or disubstituted by fluorine, chlorine, cyano, nitro, methyl, ethyl, methoxy, trifluoromethyl or trifluoromethoxy, and, wherein in the salt of formula (III')

D represents nitrogen or phosphorus, $R^{26}$, $R^{27}$, $R^{28}$ and $R^{29}$ independently of one another represent hydrogen or, in each case, optionally substituted $C_1$-$C_8$-alkyl, or mono- or polyunsaturated, optionally substituted $C_1$-$C_8$-alkylene, the optional substituents being selected from the group consisting of halogen, nitro, cyano and combinations thereof, n represents 1, 2, 3 or 4, and $R^{30}$ represents an organic or inorganic anion.

2. The composition of claim 1, further comprising at least one penetrant.

3. A method of controlling harmful insects, spider mites, unwanted vegetation, or any combination thereof, comprising applying an effective amount of the composition of claim 1, to the insects, their habitat, the spider mites, their habitat, the unwanted vegetation, or any combination thereof.

4. A spray liquor, comprising water and the composition of claim 1.

5. The spray liquor of claim 4, further comprising a penetrant.

6. A method of protecting crops, comprising applying the composition of claim 1 to the crops.

7. The composition of claim 1, wherein in the salt of formula (III'), D represents nitrogen.

8. (Withdrawn, Currently amended) The composition of claim 1, wherein in the salt of formula (III'), D represents phosphorus.

9. The composition of claim 1, wherein the salt of formula (III') is ammonium sulphate, diammonium hydrogenphosphate, or a combination thereof.

10. The composition of claim 1, wherein in the compound of formula (I), G represents hydrogen.

* * * * *